(12) United States Patent
Lee et al.

(10) Patent No.: US 11,541,144 B2
(45) Date of Patent: Jan. 3, 2023

(54) REFRIGERATOR

(71) Applicant: Samsung Electronics Co., Ltd., Suwon-si (KR)

(72) Inventors: Sang Hoon Lee, Suwon-si (KR); Jee Yong Kim, Suwon-si (KR); Joo Yeon Park, Suwon-si (KR); Myung Ju Shin, Suwon-si (KR); Hong Kwan Cho, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 245 days.

(21) Appl. No.: 16/750,312

(22) Filed: Jan. 23, 2020

(65) Prior Publication Data

US 2020/0237951 A1 Jul. 30, 2020

(30) Foreign Application Priority Data

Jan. 25, 2019 (KR) ........................ 10-2019-0009618

(51) Int. Cl.
*A61L 9/18* (2006.01)
*F25D 17/04* (2006.01)

(52) U.S. Cl.
CPC .............. *A61L 9/18* (2013.01); *F25D 17/042* (2013.01); *A61L 2209/12* (2013.01); *A61L 2209/14* (2013.01); *F25D 2317/0415* (2013.01)

(58) Field of Classification Search
CPC ... A61L 9/18; A61L 9/20; A61L 9/205; A61L 2209/12; A61L 2209/14; F25D 17/042;
(Continued)

(56) References Cited

U.S. PATENT DOCUMENTS

2002/0037244 A1 3/2002 Takahashi et al.
2012/0204581 A1 8/2012 Kang et al.
(Continued)

FOREIGN PATENT DOCUMENTS

EP 2 144 021 A1 1/2010
JP 2002-228353 8/2002
(Continued)

OTHER PUBLICATIONS

Machine translation of KR 10-2014-0124659 (Year: 2014).*
(Continued)

*Primary Examiner* — Timothy C Cleveland
(74) *Attorney, Agent, or Firm* — Staas & Halsey LLP

(57) ABSTRACT

A refrigerator includes a deodorizer installed on an upper surface of a storage compartment. The deodorizer includes a housing in which a flow path is provided, a suction port provided on a lower surface of the housing to suck air, a discharge port provided in the front of the suction port to discharge air, a photocatalytic deodorizing filter disposed at an inner side of the suction port, and a filter light source configured to irradiate light to the photocatalytic deodorizing filter, the flow path is configured to guide air from a rear lower side where the suction port is positioned to a front lower side where the discharge port is positioned, and the filter light source is disposed above the photocatalytic deodorizing filter to face the photocatalytic deodorizing filter in a state of being spaced apart from each other, and positioned above air passing through the flow path.

6 Claims, 8 Drawing Sheets

(58) Field of Classification Search
CPC ..... F25D 2317/0415; F25D 2317/0416; F25D 2317/0417
See application file for complete search history.

(56) References Cited

U.S. PATENT DOCUMENTS

2018/0238613 A1 8/2018 Choi et al.
2019/0374670 A1* 12/2019 Liu .................. A61L 9/205

FOREIGN PATENT DOCUMENTS

| | | |
|---|---|---|
| JP | 2009-30917 | 2/2009 |
| JP | 2009-30925 | 2/2009 |
| JP | 2018-59640 | 4/2018 |
| KR | 10-2010-0078791 | 7/2010 |
| KR | 10-2014-0124659 | 10/2014 |
| KR | 10-2015-0014815 | 2/2015 |

OTHER PUBLICATIONS

International Search Report dated May 25, 2020 in International Patent Application No. PCT/KR2020/001048.
Extended European Search Report dated Jan. 4, 2022 from European Application No. 20745654.2.

* cited by examiner

REFRIGERATOR

CROSS-REFERENCE TO RELATED APPLICATIONS

This application is based on and claims priority under 35 U.S.C. § 119 to Korean Patent Application No. 10-2019-0009618, filed on Jan. 25, 2019, in the Korean Intellectual Property Office, the disclosure of which is incorporated by reference herein in its entirety.

BACKGROUND

1. Field

The disclosure relates to a refrigerator including a deodorizer for removing odors.

2. Description of the Related Art

A refrigerator is an appliance that may store food in a frozen mode or a refrigerated mode by including a storage compartment for storing food and components constituting a refrigeration cycle to supply cold air generated from an evaporator of the refrigeration cycle to the storage compartment.

Because various foods are stored in the storage compartment of the refrigerator, an odor is generated from the foods in the storage compartment. Thus, the refrigerator includes a deodorizer for removing the odor generated in the storage compartment.

The deodorizer includes a housing forming a flow path through which air passes, a deodorizing filter disposed on the flow path and through which air passes, and a fan for blowing air in the storage compartment to the deodorizing filter.

Recently, a deodorizer including a light deodorizing filter for removing odors in response to light and a light source for irradiating light to the light deodorizing filter is used.

SUMMARY

It is an aspect of the disclosure to provide a deodorizer through which air may be easily passed and a refrigerator including the same.

Additional aspects of the disclosure will be set forth in part in the description which follows and, in part, will be obvious from the description, or may be learned by practice of the disclosure.

In accordance with an aspect of the disclosure, a refrigerator includes a main body in which a storage compartment is provided, and a deodorizer disposed inside the storage compartment, wherein the deodorizer includes a housing in which a flow path is provided, a suction port provided on a lower surface of the housing to suck air, a discharge port provided in the front of the suction port to discharge air, a photocatalytic deodorizing filter disposed at an inner side of the suction port, and a filter light source configured to irradiate light to the photocatalytic deodorizing filter, wherein the flow path is configured to guide air from a rear lower side where the suction port is positioned to a front lower side where the discharge port is positioned, and wherein the filter light source is disposed above the photocatalytic deodorizing filter to face the photocatalytic deodorizing filter in a state of being spaced apart from each other, and positioned above air passing through the flow path.

The filter light source includes a substrate formed in a rectangular plate shape extending from side to side and a plurality of light emitting diodes disposed to be spaced apart from side to side on a lower surface of the substrate, and the substrate is positioned above air passing through the flow path.

The housing includes an upper housing and a lower housing coupled to each other up and down to form the flow path.

The deodorizer further includes four of light source supports protruding from an upper surface of the lower housing to support front and rear ends of opposite sides of the substrate, and each of four of the light source supports includes a seating groove in which the lower surface of the substrate is seated.

At least some of four of the light source supports include a locking protrusion provided at an upper end thereof to prevent an end of the substrate seated in the seating groove from being separated from the seating groove.

The locking protrusion is formed only on two of the light source supports disposed diagonally from each other among four of the light source supports.

The deodorizer further includes a fan assembly disposed on the flow path to flow air along the flow path.

The assembly is configured to discharge air in a direction inclined toward the front lower side.

The upper housing includes a guide portion formed to be bent upward and an upper flow path portion protruding from a lower surface of the upper housing and provided at opposite sides and the front about the guide portion, and the lower housing includes a lower flow path portion protruding from an upper surface of the lower housing and provided in front, rear, left and right about the discharge port.

The upper flow path portion is formed such that an up-down width thereof increases from the rear toward the front, and the lower flow path portion is formed such that an up-down width thereof increases from the rear toward the front.

The housing further includes a suction grill formed in a grid shape on the suction port, and a lower surface of the photocatalytic deodorizing filter is spaced apart from an upper end of the suction grill.

In accordance with another aspect of the disclosure, a refrigerator includes a main body in which a storage compartment is provided, and a photocatalyst deodorizer disposed inside the storage compartment, wherein the photocatalyst deodorizer includes a housing in which a flow path is provided, a suction port provided on a lower surface of the housing to suck air, a photocatalytic deodorizing filter disposed at an inner side of the suction port, and a filter light source disposed above the photocatalytic deodorizing filter to be spaced apart from each other, wherein the filter light source includes a substrate formed in a rectangular plate shape extending from side to side and a plurality of light emitting diodes disposed to be spaced apart from side to side on a lower surface of the substrate, wherein the photocatalyst deodorizer further includes four of light source protruding from an inner lower surface of the housing to support front and rear ends of opposite sides of the substrate, and wherein each of four of the light source supports includes a seating groove in which the lower surface of the substrate is seated.

In accordance with another aspect of the disclosure, a refrigerator includes a main body in which a storage compartment is provided, and a photocatalyst deodorizer disposed inside the storage compartment, wherein the photocatalyst deodorizer includes a housing in which a flow path is provided, a suction port provided on a lower surface of the housing to suck air, a photocatalytic deodorizing filter disposed at an inner side of the suction port, and a suction grill formed in a grid shape on the suction port, and a lower surface of the photocatalytic deodorizing filter is spaced apart from an upper end of the suction grill.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Configurations shown in the embodiments and the drawings described in the present specification are only the preferred embodiments of the present disclosure, and thus it is to be understood that various modified examples, which may replace the embodiments and the drawings described in the present specification, are possible when filing the present application.

Like reference numbers or signs in the various figures of the application represent parts and components that perform substantially the same functions.

The terms used in the present specification are used to describe the embodiments of the present disclosure. Accordingly, it should be apparent to those skilled in the art that the following description of exemplary embodiments of the present invention is provided for illustration purpose only and not for the purpose of limiting the invention as defined by the appended claims and their equivalents. It is to be understood that the singular forms "a," "an," and "the" include plural referents unless the context clearly dictates otherwise. It will be understood that when the terms "includes," "comprises," "including," and/or "comprising," when used in this specification, specify the presence of stated features, figures, steps, components, or combination thereof, but do not preclude the presence or addition of one or more other features, figures, steps, components, members, or combinations thereof.

The terms "front end," "rear end," "upper portion," "lower portion," "upper end" and "lower end" used in the present specification are defined with reference to the drawings, and the shape and position of each component are not limited by these terms.

Hereinafter, a refrigerator according to an embodiment of the disclosure will be described in detail with reference to the accompanying drawings.

Figure 1:
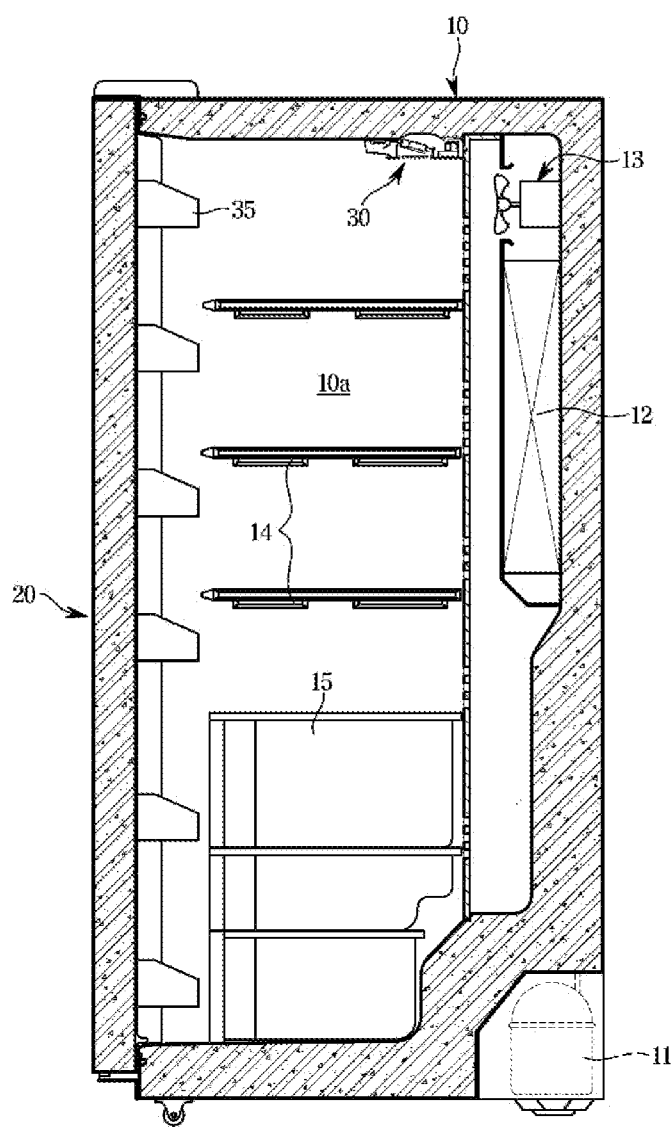
FIG. 1 is a cross-sectional view of a refrigerator according to the disclosure.

As shown in FIG. 1, a refrigerator according to an embodiment of the disclosure includes a main body 10 having an open front surface to form a storage compartment 10a, and a door 20 whose one end is rotatably coupled to the front surface of the main body 10 to open and close the storage compartment 10a.

The refrigerator also includes components of the refrigeration cycle such as a compressor 11, a condenser (not shown), an evaporator 12, and an expansion valve (not shown), and supplies cold air generated in the evaporator 12 to the storage compartment 10a through a blower 13 so that the storage compartment 10a is kept at a low temperature.

The refrigerator also includes a plurality of shelves 14 arranged to be spaced up and down in the storage compartment 10a and partitioning the storage compartment 10a up and down, and a storage drawer 15 installed at a lower portion of the storage compartment 10a to be movable back and forth to store vegetables and the like.

The refrigerator also includes a deodorizer 30 configured to remove odors generated from foods stored in the storage compartment 10a. The deodorizer 30 is installed at a rear side of an upper surface of the storage compartment 10a.

Figure 2:
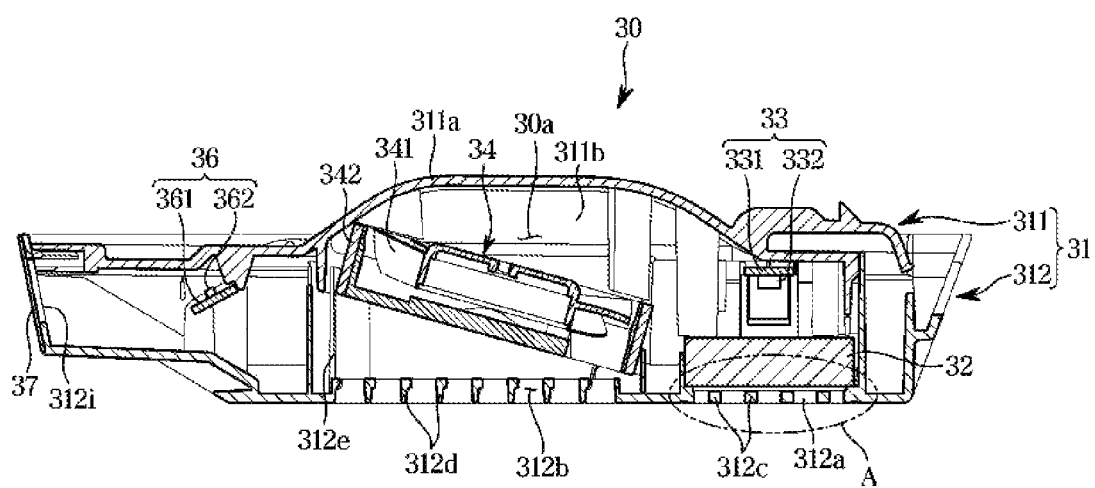
FIG. 2 is a perspective view of a deodorizer applied to a refrigerator according to an embodiment of the disclosure.
Figure 3:
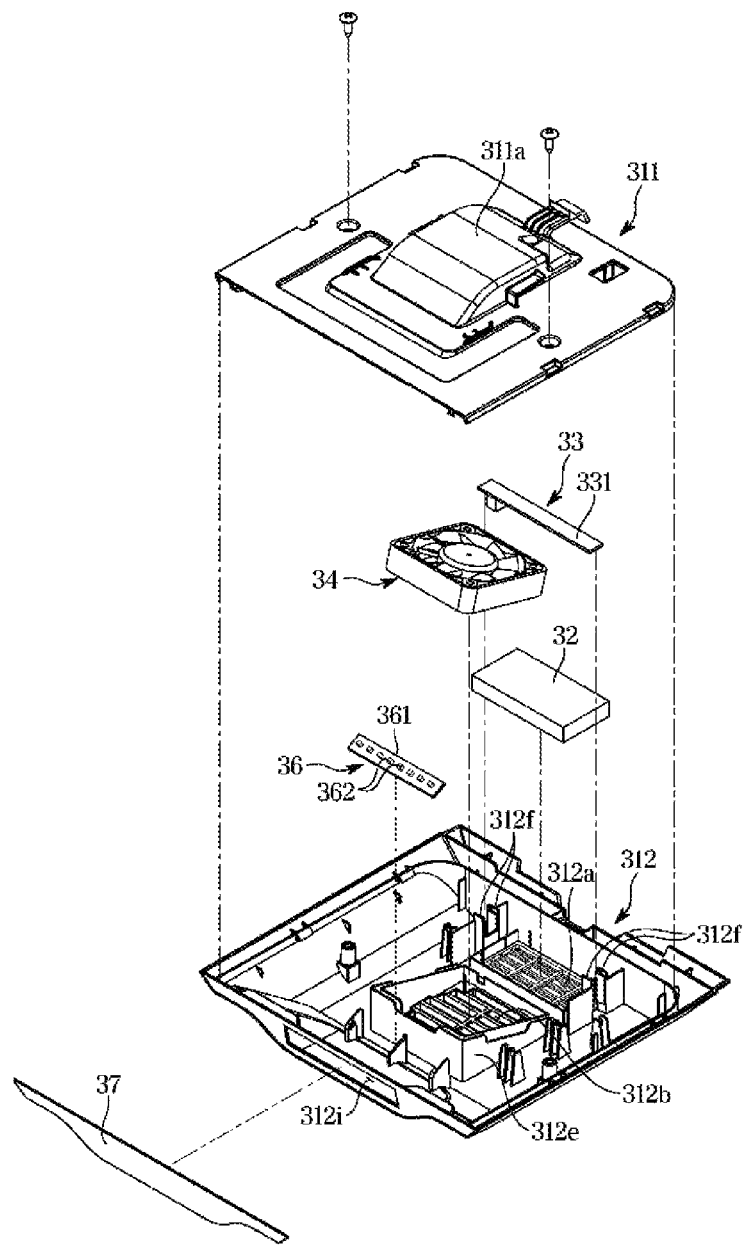
FIG. 3 is an exploded perspective view of the deodorizer applied to the refrigerator according to an embodiment of the disclosure.
Figure 4:
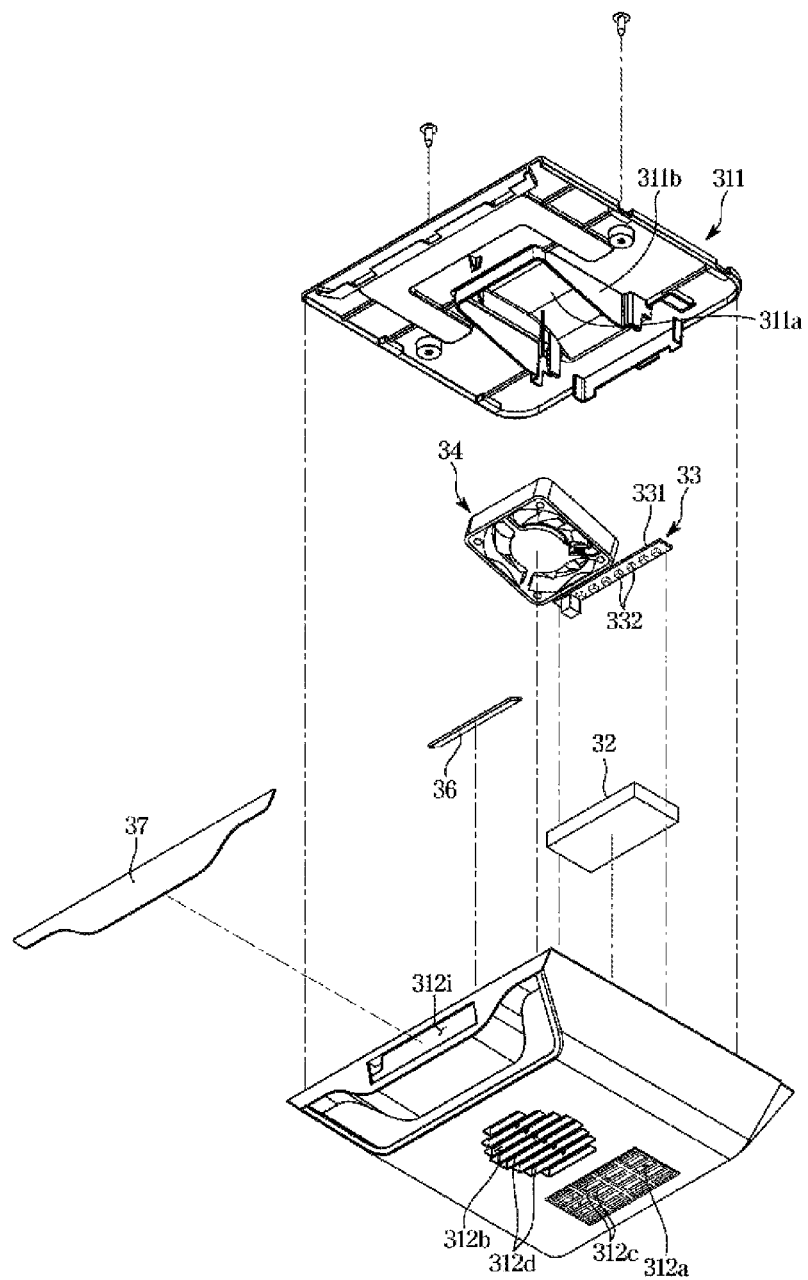
FIG. 4 is a bottom exploded perspective view of the deodorizer applied to the refrigerator according to an embodiment of the disclosure.

As shown in FIGS. 2 to 4, the deodorizer 30 includes a housing 31 forming a flow path 30a through which air passes, and a photocatalytic deodorizing filter 32 disposed on the flow path 30a inside the housing 31 and configured to react photochemically by light to remove odors, a filter light source 33 configured to generate light to irradiate the light to the photocatalytic deodorizing filter 32, and a fan assembly 34 configured to pass air in the storage compartment 10a through the flow path 30a inside the housing 31 and the photocatalytic deodorizing filter 32 disposed on the flow path 30a.

The housing 31 includes an upper housing 311 and a lower housing 312 coupled to each other up and down to form the flow path 30a.

The upper housing 311 is installed on the upper surface of the storage compartment 10a. The upper housing 311 includes a guide portion 311a formed to be bent upward to guide air, and an upper flow path portion 311b protruding from a lower surface of the upper housing 311.

The guide portion 311a serves to guide air such that a flow direction of the air may be gradually changed toward a front lower side.

The upper flow path portion 311b is provided in a rib shape at opposite sides and the front about the guide portion 311a. The upper flow path portion 311b forms the flow path 30a together with a lower flow path portion 312e of the lower housing 312 which will be described later. The upper flow path portion 311b is formed such that an up-down width thereof decreases from the rear toward the front.

The lower housing 312 includes a suction port 312a to allow air to be introduced to the flow path 30a inside the housing 31, a discharge port 312b to allow air passed through the photocatalytic deodorizing filter 32 to be discharged back into the storage compartment 10a, and the lower flow path portion 312e protruding from an upper surface of the lower housing 312.

The suction port 312a is formed in a rectangular shape extending from side to side, and a suction grill 312c of a grid shape is formed on the suction port 312a. The discharge port 312b is formed in a circular shape, and a discharge grill 312d of a bar shape is formed on the discharge port 312b. The flow path 30a guides the air sucked through the suction port 312a positioned at a rear lower side to a front lower side where the discharge port 312b is provided.

The lower housing 312 includes the lower flow path portion 312e protruding downward from the upper surface thereof to form the flow path 30a. The lower flow path portion 312e is provided in a rib form in front, rear, left, and right about the discharge port 312b.

The fan assembly 34 is installed in the lower flow path portion 312e and formed such that an up-down width thereof increases from the rear toward the front.

Accordingly, when the upper housing 311 and the lower housing 312 are coupled to each other in a state where the fan assembly 34 is installed in the lower flow path portion 312e, a lower end of the upper flow path portion 311b and an upper end of the lower flow path portion 312e are engaged with each other to form the flow path 30a, and the fan assembly 34 is disposed inside the flow path 30a.

The photocatalytic deodorizing filter 32 removes odors in air through a photochemical reaction when light is irradiated. The photocatalytic deodorizing filter 32 is disposed inside the suction port 312a, that is, above the suction port 312a in the drawing. The photocatalytic deodorizing filter 32 is formed in a rectangular parallelepiped shape to correspond to the suction port 312a.

Figure 6:
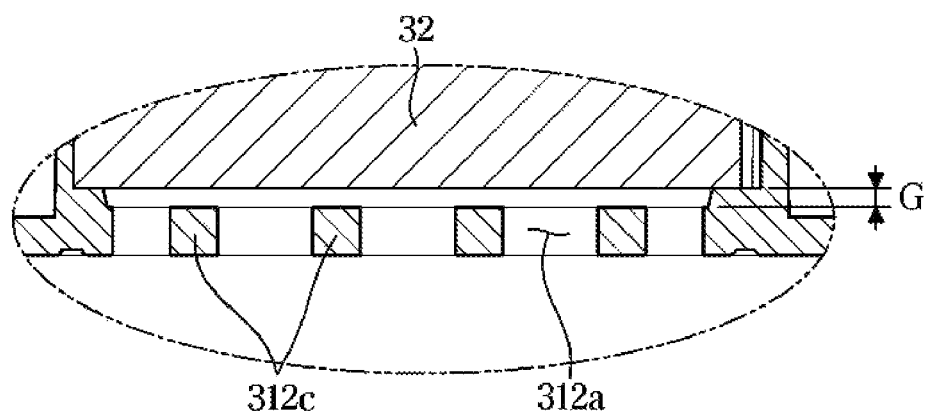
FIG. 6 is an exploded perspective view showing installation of a light source in the refrigerator according to an embodiment of the disclosure.

As shown in FIG. 6, a lower surface of the photocatalytic deodorizing filter 32 is disposed to be spaced apart from the suction grill 312c by a predetermined gap G so that air may also flow through a gap between the suction grill 312c and the lower surface of the photocatalytic deodorizing filter 32. This is to allow air to pass also through a region of the photocatalytic deodorizing filter 32 corresponding to the suction grill 312c.

As shown in FIGS. 2 and 4, the filter light source 33 is disposed to face an upper surface of the photocatalytic deodorizing filter 32 in a state of being spaced apart from each other. Accordingly, the air passed through the photocatalytic deodorizing filter 32 may flow forward through a space between the filter light source 33 and the photocatalytic deodorizing filter 32.

The filter light source 33 includes a substrate 331 formed in a rectangular shape extending from side to side, and a plurality of light emitting diodes 332 disposed to be spaced apart from side to side on a lower surface of the substrate 331.

The substrate 331 of the filter light source 33 has a left-right width corresponding to the photocatalytic deodorizing filter 32 and is disposed to correspond to a central portion in the front-rear direction of the photocatalytic deodorizing filter 32. Therefore, the light generated from the light emitting diodes 332 is distributedly irradiated symmetrically in the front-back direction on the upper surface of the photocatalytic deodorizing filter 32.

As described above, the filter light source 33 is disposed above the photocatalytic deodorizing filter 32 in a state of being spaced apart from each other and the flow path 30a guides air sucked from the rear lower side to the front lower side, the filter light source 33 is configured to be positioned above air flowing along the flow path 30a. Therefore, the filter light source 33 hardly affects the air flowing along the flow path 30a, so that the increase in flow path resistance by the filter light source 33 is prevented.

A larger amount of air may pass through the deodorizer 30 by preventing the increase in flow path resistance through the arrangement of the filter light source 33 described above, thereby improving the performance of the deodorizer 30.

As shown in FIG. 6, the lower housing 312 includes light source supports 312f supporting the filter light source 33. The light source supports 312f are formed to protrude upward from an inner lower surface of the housing 31, that is, the upper surface of the lower housing 312. A total of four of the light source supports 312f are formed to correspond to front and rear ends of opposite sides of the substrate 331 of the filter light source 33.

Figure 7:
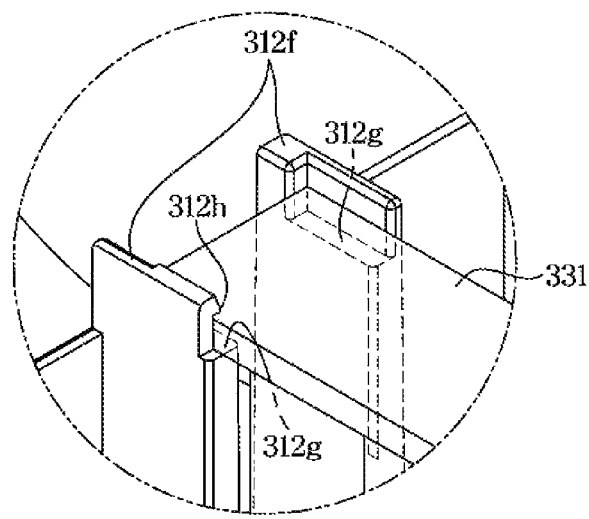
FIG. 7 is an enlarged view of a portion B of FIG. 5.
Figure 8:
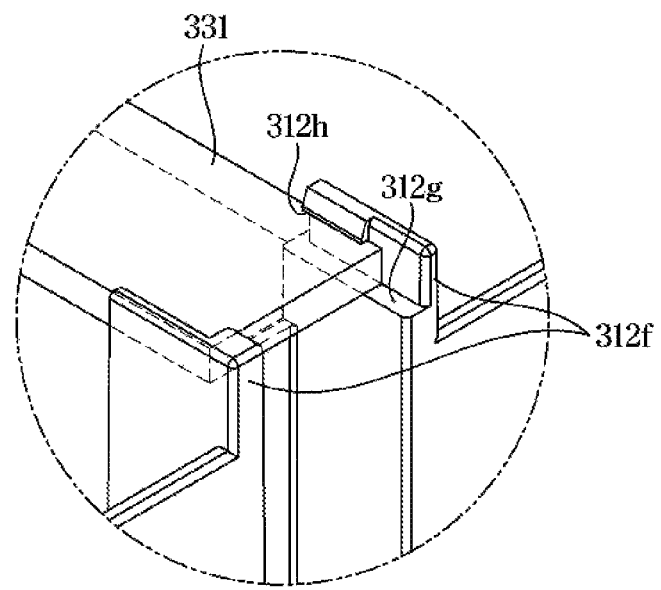
FIG. 8 is an enlarged view of a portion C of FIG. 5.

As shown in FIGS. 7 and 8, the light source supports 312f include a seating groove 312g in which each of the front and rear ends of the opposite sides of the substrate 331 of the filter light source 33 is seated, and a locking protrusion 312h provided at an upper end of the light source support 312f to prevent an end of the substrate 331 seated in the seating groove 312g from being separated from the seating groove 312g.

The seating groove 312g is provided on each of the light source supports 312f, and the locking protrusion 312h is formed only on two of the light source supports 312f disposed diagonally from each other among four of the light source supports 312f. This is to allow the substrate 331 to be seated in the seating grooves 312g by easily passing a portion where the locking protrusion 312h is formed.

The fan assembly 34 is configured by modularizing a rotating fan 341, a motor (not shown) for rotating the fan 341, and a frame 342 for supporting the fan 341 and the motor.

The fan assembly 34 is configured to discharge air in a direction inclined toward the front lower side. This is to consider that the cold air supplied through the refrigeration cycle is mainly supplied to a rear side of the storage compartment 10a. That is, because the deodorizer 30 is disposed on the rear side of the upper surface of the storage compartment 10a, the deodorizer 30 sucks low-temperature air from a rear space of the storage compartment 30a and discharges the sucked air in the direction inclined toward the front lower side. Therefore, the front space of the storage compartment 10a may also be efficiently cooled by the air discharged from the deodorizer 30.

Figure 5:
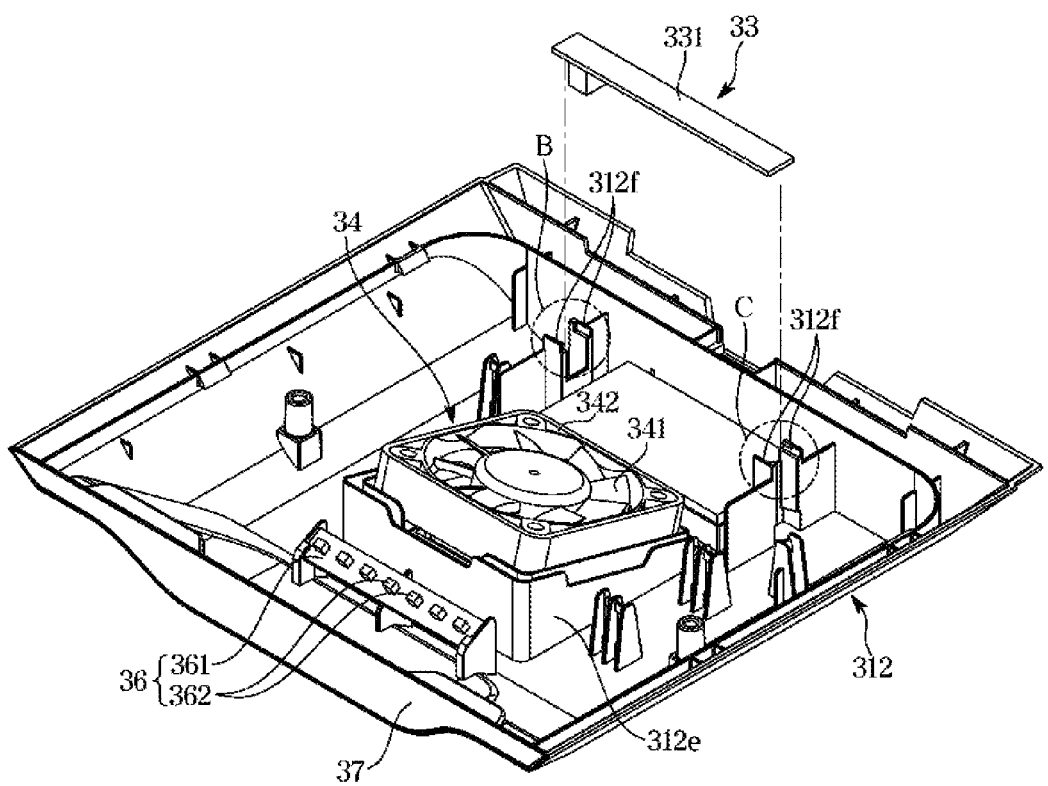
FIG. 5 is an enlarged view of a portion A of FIG. 2.

As shown in FIGS. 2 and 5, the deodorizer 30 further includes an illumination light source 36, and the housing 31 includes a through hole 312i provided at a front end thereof to allow light emitted from the illumination light source 36 to pass therethrough, and a transparent window 37 installed to cover the through hole 312i.

The illumination light source 36 includes a substrate 361 and a plurality of light emitting diodes 362 mounted on the substrate 361. Accordingly, light generated from the light emitting diode 362 is irradiated to a front side of the deodorizer 30 through the transparent window 37.

As described above, the deodorizer 30 is installed on the upper surface of the storage compartment 10a, but is not limited thereto. For example, the deodorizer 30 may be installed on a rear surface or a sidewall of the storage compartment 10a.

As is apparent from the above, a deodorizer according to an embodiment of the disclosure and a refrigerator including the same can prevent an increase in flow path resistance caused by a light source for a deodorizing filter because the light source for the deodorizing filter is not only disposed to face the deodorizing filter, but also positioned above air passing through the flow path.

Although a few embodiments of the disclosure have been shown and described, it would be appreciated by those skilled in the art that changes may be made in these embodiments without departing from the principles and spirit of the disclosure in the scope of which is defined in the claims and their equivalents.

What is claimed is:

1. A refrigerator comprising:
a main body including a storage compartment, and a deodorizer disposed inside the storage compartment, wherein the deodorizer comprises:

a housing including an upper housing and a lower housing coupled to each other to form a flow path, a suction port provided on a lower surface of the housing to draw air into the housing and a discharge port provided to discharge the air, the flow path being configured to guide the air from the suction port to the discharge port, a fan assembly disposed on the flow path to move the air along the flow path, a photocatalytic deodorizing filter disposed at an inner side of the suction port, four light source supports formed to protrude from an upper surface of the lower housing, a filter light source configured to irradiate light to the photocatalytic deodorizing filter, and wherein the filter light source comprises:

a substrate and a plurality of light emitting diodes spaced apart on a lower surface of the substrate and disposed to face an upper surface of the photocatalytic deodorizing filter and spaced apart from the photocatalytic deodorizing filter by supporting front and rear ends of opposite sides of the substrate by the four light source supports, and wherein the filter light source is configured to face the upper surface of the photocatalytic deodorizing filter spaced apart from the photocatalytic deodorizing filter such that the air passes through a suction grill of the housing formed on the suction port, a predetermined gap and the flow path between the filter light source and the photocatalytic deodorizing filter, wherein a lower surface of the photocatalytic deodorizing filter is spaced apart from an upper end of the suction grill by the predetermined gap, wherein the lower housing comprises a lower flow path portion provided in a rib form and formed to protrude from the upper surface of the lower housing around the discharge port, and wherein the fan assembly is installed in the lower flow path portion.

2. The refrigerator according to claim 1, wherein each of the four light source supports comprises a seating groove in which the lower surface of the substrate is seated.

3. The refrigerator according to claim 2, wherein at least some of the four light source supports comprise a locking protrusion provided at an upper end thereof to prevent an end of the substrate seated in the seating groove from being separated from the seating groove.

4. The refrigerator according to claim 3, wherein the locking protrusion is formed only on two of the light source supports disposed diagonally from each other among the four light source supports.

5. The refrigerator according to claim 1, wherein the fan assembly is configured to discharge air in a direction inclined toward the discharge port.

6. The refrigerator according to claim 1, wherein the upper housing comprises a guide portion formed with an upward bend and an upper flow path portion protruding from a lower surface of the upper housing and provided at opposite sides and a front of the guide portion.

* * * * *